(12) United States Patent
De Picciotto et al.

(10) Patent No.: US 11,358,007 B2
(45) Date of Patent: Jun. 14, 2022

(54) ULTRASOUND FREQUENCY AND MICROBUBBLE SIZE OPTIMIZATION IN MICROBUBBLE-ENHANCED ULTRASOUND TREATMENT

(71) Applicant: INSIGHTEC, LTD., Tirat Carmel (IL)

(72) Inventors: Rafi De Picciotto, Tirat Carmel (IL); Javier Grinfeld, Tel Aviv-Jaffa (IL); Yoav Levy, Hinanit (IL)

(73) Assignee: INSIGHTEN, LTD., Tirat Carmel (IL)

(*) Notice: Subject to any disclaimer, the term of this patent is extended or adjusted under 35 U.S.C. 154(b) by 420 days.

(21) Appl. No.: 16/622,004

(22) PCT Filed: Jun. 29, 2018

(86) PCT No.: PCT/IB2018/000841
§ 371 (c)(1),
(2) Date: Dec. 12, 2019

(87) PCT Pub. No.: WO2019/002947
PCT Pub. Date: Jan. 3, 2019

(65) Prior Publication Data
US 2021/0146156 A1 May 20, 2021

Related U.S. Application Data

(63) Continuation-in-part of application No. 15/637,163, filed on Jun. 29, 2017, now Pat. No. 11,123,575.
(Continued)

(51) Int. Cl.
*A61N 7/00* (2006.01)
*A61N 5/10* (2006.01)
(Continued)

(52) U.S. Cl.
CPC ........... *A61N 5/1049* (2013.01); *A61B 5/489* (2013.01); *A61B 34/10* (2016.02);
(Continued)

(58) Field of Classification Search
CPC .......... A61N 5/00; A61N 5/10; A61N 5/1049; A61N 5/1064; A61N 5/103; A61N 5/1048;
(Continued)

(56) References Cited

U.S. PATENT DOCUMENTS

2007/0016039 A1 1/2007 Vortman et al.
2008/0221382 A1 9/2008 Karshafian et al.
(Continued)

FOREIGN PATENT DOCUMENTS

CN 105682739 A 6/2016
EP 2343103 A1 7/2011
(Continued)

OTHER PUBLICATIONS

International Search Report and Written Opinion of the International Searching Authority dated Nov. 19, 2018 for International Application No. PCT/IB18/000841 (13 pages).
(Continued)

*Primary Examiner* — Jurie Yun
(74) *Attorney, Agent, or Firm* — Morgan, Lewis & Bockius LLP (57) ABSTRACT

Various approaches for enhancing treatment of target tissue using a source of focused ultrasound while limiting damage to non-target tissue include selecting a frequency of ultrasound waves transmitted from the source of focused ultrasound for generating a focus in the target tissue; providing microbubbles having the first size distribution such that at least 50% of the microbubbles have a radius smaller than a critical radius corresponding to a resonance frequency matching the selected frequency of ultrasound waves; and applying the ultrasound waves at the selected frequency to treat the target tissue.

23 Claims, 4 Drawing Sheets

Related U.S. Application Data (60) Provisional application No. 62/597,073, filed on Dec. 11, 2017, provisional application No. 62/597,076, filed on Dec. 11, 2017, provisional application No. 62/526,545, filed on Jun. 29, 2017, provisional application No. 62/526,550, filed on Jun. 29, 2017, provisional application No. 62/526,548, filed on Jun. 29, 2017.

(51) Int. Cl.
| | |
|---|---|
| *A61B 5/00* | (2006.01) |
| *A61N 7/02* | (2006.01) |
| *A61B 34/10* | (2016.01) |
| *A61M 37/00* | (2006.01) |
| *A61B 6/12* | (2006.01) |
| *A61B 6/03* | (2006.01) |
| *A61B 6/00* | (2006.01) |

(52) U.S. Cl.
CPC ......... *A61M 37/0092* (2013.01); *A61N 5/103* (2013.01); *A61N 5/1039* (2013.01); *A61N 5/1048* (2013.01); *A61N 5/1064* (2013.01); *A61N 7/00* (2013.01); *A61N 7/02* (2013.01); *A61B 5/4836* (2013.01); *A61B 6/03* (2013.01); *A61B 6/12* (2013.01); *A61B 6/504* (2013.01); *A61B 2034/104* (2016.02); *A61B 2034/105* (2016.02); *A61N 2005/1055* (2013.01); *A61N 2005/1087* (2013.01); *A61N 2005/1098* (2013.01); *A61N 2007/0039* (2013.01)

(58) Field of Classification Search
CPC ........ A61N 5/1039; A61N 5/489; A61N 7/00; A61N 7/02; A61N 2005/1052; A61N 2005/1055; A61N 2005/1058; A61N 2005/1061; A61N 2005/1087; A61N 2005/1092; A61N 2005/1098; A61N 2007/0004; A61N 2007/0039; A61B 5/00; A61B 5/4836; A61B 5/489; A61B 34/10; A61B 6/03; A61B 6/12; A61B 6/504; A61B 2034/104; A61B 2034/105; A61M 37/00; A61M 37/0092

See application file for complete search history.

(56) References Cited

U.S. PATENT DOCUMENTS

| | | | | |
|---|---|---|---|---|
| 2012/0116221 | A1* | 5/2012 | Sehgal | A61N 7/00 600/439 |
| 2013/0331738 | A1 | 12/2013 | Borrelli | |
| 2014/0343421 | A1 | 11/2014 | Kim et al. | |
| 2014/0378737 | A1 | 12/2014 | Carpenter et al. | |
| 2015/0196638 | A1 | 7/2015 | Czarnota et al. | |
| 2020/0323515 | A1* | 10/2020 | Levy | A61B 8/4416 |
| 2021/0187331 | A1* | 6/2021 | Zadicario | A61M 37/0092 |

FOREIGN PATENT DOCUMENTS

| | | |
|---|---|---|
| WO | WO2010118307 A1 | 10/2010 |
| WO | WO2013034709 A1 | 3/2013 |
| WO | WO2014118632 A1 | 8/2014 |

OTHER PUBLICATIONS

International Search Report and Written Opinion of the International Searching Authority dated Nov. 28, 2018 for International Application No. PCT/IB18/000811 (12 pages).
International Search Report and Written Opinion of the International Searching Authority dated Nov. 12, 2018 for International Application No. PCT/IB18/00834 (12 pages).
Extended European Search Report, EP18180302.4, dated Nov. 21, 2018, 5 pgs.
Decision to Grant, EP18180302, dated Jan. 30, 2020, 2 pgs.
Decision to Grant, EP18768933, dated Jul. 1, 2021, 3 pgs.
Insightec, Ltd., Allowance Notification for Invention, CN201880043567.3, dated Jan. 30, 2022, 2 pgs.
Vlacos, F. et al., "Pernuability Assessment of the Focused Untrasound-Induced Blood-Brain Barrier Opening Using Dynamic Contrast-Enchanced MRI," Phys. Med. Biol. 55 (2010) 5451-5466, 16 pages.
Vortman, Office Action, U.S. Appl. No. 15/637,163, dated May 13, 2019, 15 pgs.
Vortman, Office Action, U.S. Appl. No. 15/637,163, dated Dec. 6, 2019, 12 pgs.
Vortman, Office Action, U.S. Appl. No. 15/637,163, dated May 21, 2020, 14 pgs.
Vortman, Final Office Action, U.S. Appl. No. 15/637,163, dated Sep. 18, 2020, 15 pgs.
Vortman, Notice of Allowance, U.S. Appl. No. 15/637,163, dated May 28, 2021, 11 pgs.
Insightec, Ltd., Communication Pursuant to Article 9 4(3), EP18759374.4 dated Sep. 20, 2021, 4 pgs.
First Office Action, CN201880056389, dated Feb. 1, 2021, 19 pgs.
Second Office Action, CN201880056389, dated Aug. 30, 2021, 19 pgs.
First Office Action, CN201880043399.8, dated Feb. 2, 2021, 7 pgs.
Notification to Grant Patent Right for Invention, CN201880043399-8, dated Aug. 30, 2021, 3 pgs.

* cited by examiner

ULTRASOUND FREQUENCY AND MICROBUBBLE SIZE OPTIMIZATION IN MICROBUBBLE-ENHANCED ULTRASOUND TREATMENT

CROSS-REFERENCE TO RELATED APPLICATION

This application is a U.S. National Phase Application of PCT/IB2018/000841, filed Jun. 29, 2018, which claims priority to, and the benefit of, U.S. Patent Application Nos. 62/526,548 (filed on Jun. 29, 2017), 62/526,545 (filed on Jun. 29, 2017), 62/526,550 (filed on Jun. 29, 2017), Ser. No. 15/637,163 (filed on June 29, 2017), 62/597,073 (filed on Dec. 11, 2017), and 62/597,076 (filed on Dec. 11, 2017). The entire disclosures of these priority documents are hereby incorporated by reference.

FIELD OF THE INVENTION

The present invention relates, generally, to microbubble-enhanced ultrasound treatment, and more particularly to systems and methods for optimizing the ultrasound frequency and microbubble size for increasing treatment efficiency of the target.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, targeted drug delivery, disruption of the blood-brain barrier (BBB), lysing of clots, and other surgical procedures. During tumor ablation, a piezoceramic transducer is placed externally to the patient, but in close proximity to the tumor to be ablated (i.e., the target region). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

During a focused ultrasound procedure, small gas bubbles (or "microbubbles") may be generated and/or introduced into the target region. Depending upon the amplitude and frequency of the applied acoustic field, the microbubbles may oscillate or collapse (a phenomenon known as "cavitation") and thereby cause various thermal effects in the target region and/or its surroundings. For example, microbubble cavitation may enhance energy absorption at the ultrasound focal region, causing the tissue therein to be heated faster and ablated more efficiently than would occur in the absence of microbubbles. If utilized in the central nervous system, microbubble cavitation may disrupt blood vessels, thereby inducing "opening" of the BBB for enhancing targeted drug delivery. As used herein, the response of microbubbles to the applied sonication is referred to as the "microbubble response," and the thermal effect in the target and/or non-target regions resulting from the sonication and/or microbubble cavitation is referred to as the "therapeutic effect."

The mechanism of microbubble oscillation/cavitation upon application of the ultrasound waves/pulses involves a resonant property of the microbubbles—i.e., the microbubbles may oscillate at a resonance frequency in response to the applied acoustic field. The microbubble resonance frequency generally depends on the sizes of the microbubbles and the properties of the ambient medium in which they are present (e.g., the viscosity of the agent, the size of a vessel, etc.). Conventionally, the transducer array is driven at a frequency equal to the microbubble resonance frequency in order to maximize the microbubble response and thereby optimize treatment efficiency. While this approach may improve treatment effects at the target region, the presence of the microbubbles in non-target regions (e.g., tissue surrounding the target region) may cause undesired collateral damage by enhancing the effects of applied ultrasound energy, resulting in injury to non-target tissue that otherwise would be clinically unaffected.

Accordingly, there is a need for improved microbubble-enhanced treatment that efficiently treats the target region while avoiding damage to the non-target tissue.

SUMMARY

The present invention relates to microbubble-enhanced ultrasound treatment that optimizes the effects of treatment based on the value of one or more ultrasound parameters (e.g., frequency and/or power) and the microbubble resonance frequency at the target region. At the resonance frequency, microbubbles will oscillate and/or collapse so as to enhance the treatment effects of applied ultrasound. The overall objective herein is to limit the microbubble response (and thereby the therapeutic effect) at non-target regions—e.g., tissues surrounding the target region and/or tissues located between the ultrasound transducer and the target region—and/or the degree of cavitation so as to eliminate (or at least reduce) collateral damage. In various embodiments, the ultrasound parameter is optimized based on characteristics (e.g., type, property, structure, thickness, density, etc.) of the target tissue and/or non-target regions as well as ultrasound-tissue interactions, such as reflection, refraction, and/or scattering at tissue interfaces and/or ultrasound propagation in tissue. In addition, the microbubble resonance frequency (based on, e.g., the mean radius of the microbubbles) may be selected to differ from the frequency of the applied ultrasound waves/pulses. Preferably, the microbubble resonance frequency is substantially larger than the ultrasound frequency (e.g., by a factor of ten), but it can be substantially smaller than the ultrasound frequency, if desired. For example, the ultrasound waves/pulses may have a frequency of 0.23 MHz, and the microbubble resonance frequency may be at 2 MHz. As a result, in an ultrasound procedure using a low acoustic power, microbubbles at the non-target region are unresponsive to (or at least have a limited response without cavitation) the relatively low acoustic field, whereas microbubbles at the target region (where the acoustic field is relatively high due to the focused beam) may oscillate and/or collapse. Accordingly, embodiments of the present invention maximize the microbubble response to applied ultrasound at the target region relative to the response within the healthy tissue surrounding the target, as well as tissues along the path between the transducer and the target region. As used herein, the terms "optimal" and "optimizing" generally involve determining/selecting the best frequency practically discernible within the limitations of clinical practice, the utilized technology and the method employed for treating the target region.

In some embodiments, the microbubble resonance frequency is controlled by selecting a size distribution of the microbubbles. Generally, the smaller the radius of the microbubbles, the larger will be their resonance frequency. Accordingly, once the ultrasound frequency is determined, the mean radius of microbubbles having a resonance frequency substantially equal to the ultrasound frequency may be determined. In one implementation, the size distribution of the microbubbles is selected such that a significant fraction (e.g., more than 50%, 90%, 95%, or 99% or more) of the microbubbles have a radius below that corresponding to a resonance frequency equal to the applied ultrasound frequency (so that the microbubble resonance frequency exceeds the applied ultrasound frequency). For example, the maximum radius of the selected microbubbles may be 50% smaller than the radius corresponding to a resonance frequency equal to the ultrasound frequency. In practice, this can be achieved by passing the microbubbles through a filter having a pore size corresponding to the selected microbubble size. The filtered microbubbles may then be introduced into the target region for enhancing ultrasound treatment. Again, these microbubbles may be unresponsive to the relatively low-power acoustic field directed at the non-target region in order to avoid (or least limit) damage to the non-target tissue, but may oscillate and/or collapse in response to the relatively high acoustic field at the target region, thereby enhancing tissue disruption at the target region.

Accordingly, in one aspect, the invention pertains to a system for enhancing treatment of target tissue while limiting damage to non-target tissue. In various embodiments, the system includes an ultrasound transducer; an administration device for providing microbubbles having the first size distribution to the target tissue; and a controller configured to (a) select a frequency of ultrasound waves transmitted from the ultrasound transducer for generating a focus in the target tissue; (b) determine the first size distribution of the microbubbles such that at least 50% of the microbubbles have a radius different from a critical radius corresponding to a resonance frequency matching the selected frequency of ultrasound waves; and (c) cause the ultrasound transducer to transmit the ultrasound waves at the selected frequency for treating the target tissue. In one implementation, the administration device includes a filter having a pore size different from the critical radius. In one embodiment, at least 99% of the provided microbubbles have a radius smaller than the critical radius. Additionally, the maximal radius of at least 50% (or, in some embodiments, 99%) of the provided microbubbles is at least 50% smaller than the critical radius. Alternatively, at least 99% of the provided microbubbles may have a radius larger than the critical radius. the minimal radius of at least 50% (or, in some embodiments, 99%) of the provided microbubbles is at least 50% larger than the critical radius.

In various embodiments, the system may further include an imaging device for acquiring characteristics of the target tissue and non-target tissue; the controller is responsive to signals from the imaging device indicative of the characteristics and is configured to select the frequency based on the signals. In addition, the non-target tissue may include intervening tissue located between the source of focused ultrasound and the target tissue; the controller may be further configured to (i) predict acoustic interactions between the ultrasound waves and the intervening tissue based on the acquired characteristics and (ii) select the frequency of ultrasound waves based at least in part on the predicted acoustic interactions. Further, the controller may be further configured to (i) cause the ultrasound transducer to sonicate the target tissue with multiple ultrasound frequencies within a test range; (ii) measure, for each frequency, a value of a parameter (e.g., a power, an energy, an intensity, an acoustic force, a tissue displacement, and/or a temperature) indicative of an amount of ultrasound energy deposited in the target tissue; and (iii) select the frequency of ultrasound waves among the frequencies within the test range based on the measured values. In one embodiment, the controller is further configured to select the frequency of ultrasound waves corresponding to the measured value that itself corresponds to a maximum amount of ultrasound energy deposited in the target tissue. In addition, the system may further include an imaging device and/or an acoustic signal detector for measuring the value of the parameter.

In some embodiments, the controller is further configured to determine a frequency range such that the selected frequency is therewithin. In addition, at least 50% of the provided microbubbles may have a radius smaller than a minimal radius corresponding to a maximal frequency within the frequency range. Alternatively, at least 50% of the provided microbubbles may have a radius larger than the maximal radius corresponding to a minimal frequency within the frequency range. In one implementation, the system further includes a detector for detecting an acoustic signal from the microbubbles. The controller can then be further configured to determine, based on the detected acoustic signal, whether a microbubble response to the ultrasound waves is above a predetermined threshold, and if so, to adjust the selected frequency and/or an intensity associated with the ultrasound waves and/or to cause the administration device to provide microbubbles having the second size distribution; radiuses of the microbubbles in the second size distribution may be smaller (or, in some embodiments, larger) than radiuses of the microbubbles in the first size distribution. In addition, the system may further include a radiation device for transmitting a radiation dose to the target tissue for treatment. In one embodiment, the administration device is further configured to administer a therapeutic agent to the target tissue for treatment. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, and/or Cytarabine (cytosine arabinoside, ara-C)/ara-U.

In another aspect, the invention relates to a method of enhancing treatment of target tissue using a source of focused ultrasound while limiting damage to non-target tissue. In various embodiments, the method includes (a) selecting a frequency of ultrasound waves transmitted from the source of focused ultrasound for generating a focus in the target tissue; (b) providing microbubbles having the first size distribution such that at least 50% of the microbubbles have a radius different from a critical radius corresponding to a resonance frequency matching the selected frequency of ultrasound waves; and (c) applying the ultrasound waves at the selected frequency to treat the target tissue. In one implementation, the method further includes filtering the microbubbles with a filter having a pore size different from the critical radius. In one embodiment, at least 99% of the provided microbubbles have a radius smaller than the critical radius. Additionally, the maximal radius of at least 50% (or, in some embodiments, 99%) of the provided microbubbles is at least 50% smaller than the critical radius. Alternatively, at least 99% of the provided microbubbles may have a radius larger than the critical radius. the minimal radius of at least 50% (or, in some embodiments, 99%) of the provided microbubbles is at least 50% larger than the critical radius.

In various embodiments, the method further includes acquiring characteristics of the target tissue and non-target tissue using, e.g., imaging data; the frequency of ultrasound waves is selected based on the acquired characteristics. In one embodiment, the non-target tissue includes intervening tissue located between the source of focused ultrasound and the target tissue. The method may further include predicting acoustic interactions between the ultrasound waves and the intervening tissue based on the acquired characteristics; the frequency of ultrasound waves is then selected based at least in part on the predicted acoustic interactions. In addition, the method may further include sonicating the target tissue with multiple ultrasound frequencies within a test range and measuring, for each frequency, a value of a parameter (e.g., a power, an energy, an intensity, an acoustic force, a tissue displacement, and/or a temperature) indicative of an amount of ultrasound energy deposited in the target tissue; the frequency of ultrasound waves is selected among the frequencies within the test range based on the measured values. In one embodiment, the selected frequency of ultrasound waves corresponds to the measured value that itself corresponds to a maximum amount of ultrasound energy deposited in the target tissue.

In some embodiments, the method further includes determining a frequency range such that the selected frequency is therewithin. In addition, at least 50% of the provided microbubbles may have a radius smaller than a minimal radius corresponding to a maximal frequency within the frequency range. Alternatively, at least 50% of the provided microbubbles may have a radius larger than the maximal radius corresponding to a minimal frequency within the frequency range. In one implementation, the method further includes detecting an acoustic signal from the microbubbles and determining whether a microbubble response to the ultrasound waves is above a predetermined threshold, and if so, adjusting the selected frequency and/or an intensity associated with the ultrasound waves, and/or providing microbubbles having the second size distribution; radiuses of the microbubbles in the second size distribution may be smaller (or, in some embodiments, larger) than radiuses of the microbubbles in the first size distribution. In addition, the method may further include exposing the target tissue to a radiation dose for treatment or administering a therapeutic agent to the target tissue for treatment. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, and/or Cytarabine (cytosine arabinoside, ara-C)/ara-U.

As used herein, the term "substantially" means±10%, and in some embodiments, ±5%. "Clinically unaffected" means having an undesired (and sometimes the lack of a desired) effect on tissue that is considered insignificant by clinicians, e.g., prior to triggering the onset of damage thereto. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
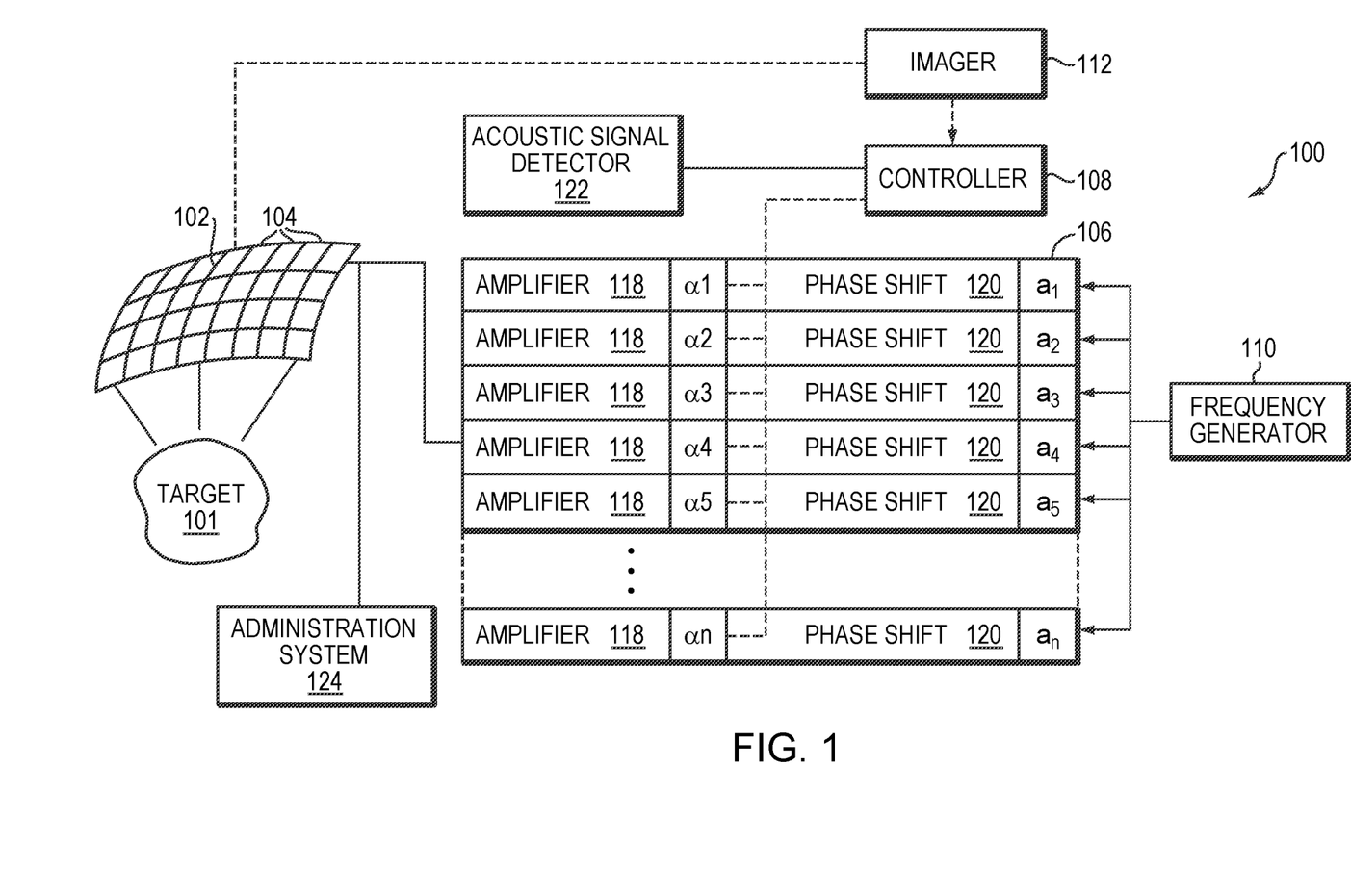
FIG. 1 schematically depicts an exemplary ultrasound system in accordance with various embodiments of the current invention.

FIG. 1 illustrates an exemplary ultrasound system 100 for generating and delivering a focused acoustic energy beam to a target region 101 within a patient's body. The applied ultrasound waves/pulses may ablate tissue in the target region and/or induce microbubble oscillation and/or cavitation to improve treatment effects. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes an imager 112, such as a magnetic resonance imaging (MRI) device, a computer tomography (CT) device, a positron emission tomography (PET) device, a single-photon emission computed tomography (SPECT) device, or an ultrasonography device, for determining anatomical characteristics (e.g., the type, property, structure, thickness, density, etc.) of the tissue at the target region 101 and/or the non-target region.

The array 102 may have a curved (e.g., spherical or parabolic) shape suitable for placing it on the surface of the patient's body, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radio frequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$, imposed by the beamformer 106 serve to transmit and focus ultrasonic energy through the intervening tissue located between the transducer elements 104 and the target region onto the target region 101, and account for wave distortions induced in the intervening tissue. The amplification factors and phase shifts are computed using the controller 108, which may provide the computational functions through software, hardware, firmware, hardwiring, or any combination thereof In various embodiments, the controller 108 utilizes a general-purpose or special-purpose digital data processor programmed with software in a conventional manner, and without undue experimentation, in order to determine the optimal value(s) of ultrasound parameter(s) (e.g., frequency, phase shift and/or amplification factor(s)) associated with each element 104 so as to generate a desired focus or any other desired spatial field patterns at the target region 101. The optimal value(s) of the ultrasound parameter(s) may be refined experimentally before, after, and/or at one or more times during the ultrasound procedure based on, for example, the focus quality, the focus location relative to the target region 101 and/or the microbubble response to the ultrasound sonications as further described below. The quality and location of the focus may be monitored using the imager 112, and the microbubble response may be detected using the transducer 102 and/or an acoustic-signal detector 122.

In certain embodiments, the optimal value(s) of the ultrasound parameter(s) is(are) computationally estimated using a physical model. For example, the physical model may predict focusing properties (e.g., the shape, size and location of the focus zone 204) based on one or more ultrasound parameters associated with each element 104, as well as information about the geometry of the transducer elements 104 and their locations and orientations relative to the target region 101. Based on the prediction, the controller 108 may determine the optimal value(s) of the ultrasound parameter(s) that generate(s) the most desired focusing properties at the target region 101. In some embodiments, the physical model includes detailed information about the characteristics of the intervening tissue and their effects (e.g., reflection, refraction, and/or scattering) on propagation of acoustic energy. Such information may be obtained from the imager 112 and/or other suitable devices. Image acquisition may be three-dimensional (3D) or, alternatively, the imager 112 may provide a set of two-dimensional (2D) images suitable for reconstructing a 3D image of the target and/or non-target regions. Image-manipulation functionality may be implemented in the imager 112, in the controller 108, or in a separate device.

In certain treatment scenarios, ultrasound waves/pulses propagating towards the target region 101 from different directions may encounter a highly variable anatomy, such as different thicknesses of tissue layers and different acoustic impedances; as a result, energy deposition at the target region 101 varies significantly and often nonmonotonically with frequency, and the optimum frequency for a particular patient is typically unpredictable. Accordingly, in some embodiments, the frequency of the ultrasound is optimized by sequentially sonicating the target region 101 with waves having different "test frequencies" within a test frequency range either prior to or during the ultrasound procedure (e.g., during treatment setup); for each tested frequency, a parameter (e.g., a temperature, an acoustic force, a tissue displacement, a power, an energy, an intensity, etc.) indicative of energy deposition in the target region 101 is measured. In addition, the measurements may be utilized to adjust parameters of the physical prediction model.

The test range may span the entire range of frequencies suitable for ultrasound treatment (e.g., in various embodiments, 0.1 MHz to 10 MHz), but is typically a much smaller sub-range thereof in which the optimal frequency is to be expected. Such a sub-range may be determined, e.g., based on estimates of the optimal frequency using the physical model, the results of computational simulations, or empirical data acquired for the same target in other patients. The frequencies to be tested may be distributed uniformly or non-uniformly over the test range. In various embodiments, the density of test frequencies increases with closer proximity to an estimated optimal frequency based on, e.g., prior experience with the same organ or tissue. The test range and the test frequencies therewithin may be predetermined, or adjusted dynamically during the optimization process. For example, in one embodiment, testing is initially performed at large frequency intervals (e.g., in steps of 20 kHz) over a large test range (e.g., from 0.1 to 10 MHz) to determine a sub-range (e.g., from 0.1 to 1 MHz) of frequencies resulting in high energy deposition at the target region 101, and the optimum frequency is thereafter determined within the sub-range by testing at smaller intervals (e.g., in steps of 5 kHz). In another embodiment, testing is performed for a sub-set of pre-determined potential test frequencies, each actual test frequency being selected from the set of potential test frequencies based on the results of previous tests.

Thus, optimizing the ultrasound frequency may involve iteratively setting a test frequency, sonicating the target region 101 at the selected frequency, and quantitatively assessing the resulting energy deposition at the target region 101. This may be accomplished using, e.g., MRI thermometry to measure the temperature increase in the target region 101 resulting from the deposited energy, MR-ARFI to measure the tissue displacement resulting from the acoustic pressure at the target region 101, ultrasound detection to measure the intensity of the ultrasound reflected from the target region 101, or generally any experimental technique for measuring a parameter that correlates with energy deposition at the target region 101 in a known and predictable manner. Following frequency optimization, the phase and/or amplitude settings of the phased-array transducer 102 may be adjusted to optimize the focus for the selected frequency. Approaches to determining an optimal frequency for the ultrasound application are provided, for example, in U.S. Patent Publication No. 2016/0008633, the contents of which are incorporated herein by reference.

In various embodiments, microbubbles are introduced intravenously or, in some cases, by injection proximate to the target region 101 using a conventional administration system 124 (e.g., a syringe, a peristaltic pump, etc.) for enhancing the ultrasound treatment. For example, the microbubbles may be introduced into the patient's brain in the form of liquid droplets that subsequently vaporize, as gas-filled bubbles, or entrained with another suitable substance, such as a conventional ultrasound contrast agent. The microbubbles may react to an applied oscillating acoustic pressure with volume pulsations. Depending on the amplitude of the ultrasound waves/pulses, microbubble oscillation will be related either linearly or nonlinearly to the applied acoustic pressure. For a low acoustic pressure, the instantaneous microbubble radius may oscillate linearly in relation to the amplitude of the applied acoustic pressure. Microbubble oscillation is governed by parameters such as the resonance frequency, damping coefficients, and shell properties. Thus, if the frequency of the applied acoustic waves/pulses is equal to the microbubble resonance frequency, the microbubbles experience a large force and can collapse. This risks damage to non-target tissue if the microbubbles are present therein.

To avoid this undesired effect, in various embodiments, the resonance frequency, $f_m$, of the microbubbles is selected to be substantially different from (e.g., ten times larger or smaller than) the selected optimal ultrasound frequency, $f_r$. In addition, the transducer elements 104 are activated to transmit waves/pulses having a low acoustic power (e.g., 5 W) during treatment. In this way, because the ultrasound waves/pulses arriving at non-target regions have a low acoustic intensity and their frequency differs substantially from the resonance frequency of the microbubbles, the microbubbles in the non-target region may be unresponsive (or have a limited response without cavitation) to the applied acoustic field. This thereby ensures that no (or at least very limited) non-target tissue is damaged. In contrast, at the target region 101, where the ultrasound beams are focused, the acoustic intensity is substantially larger than outside the target region and may be sufficient to cause the microbubbles to oscillate and/or collapse. This will enhance energy absorption at the target region 101 for tissue ablation and/or cause disruption of blood vessels for targeted drug delivery.

Figure 2:
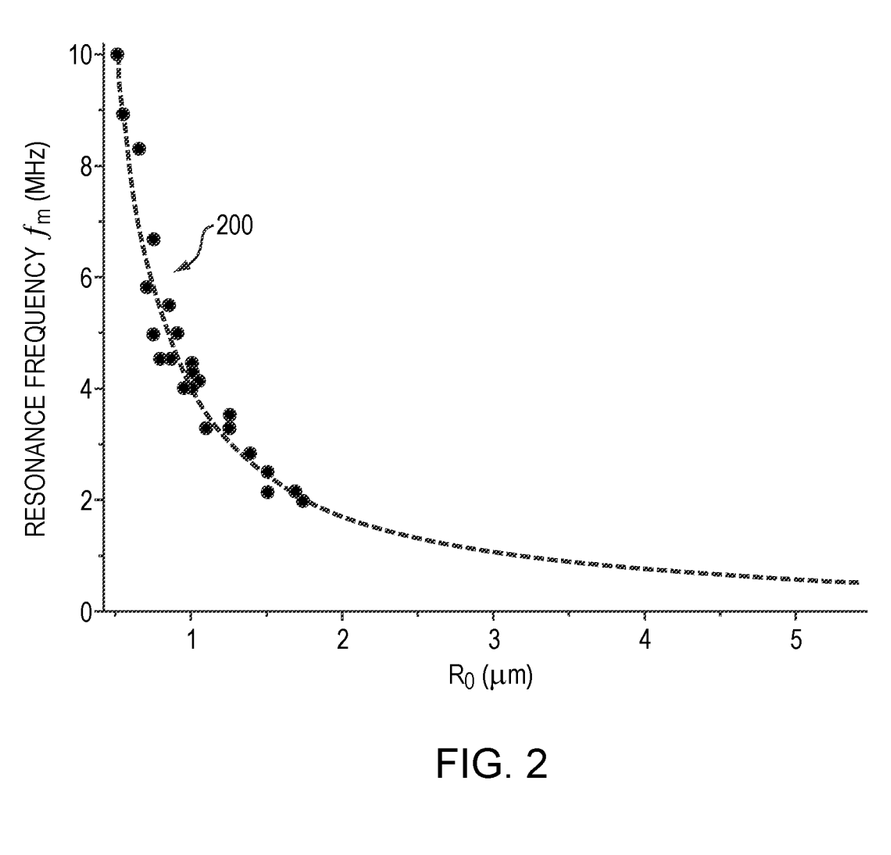
FIG. 2 depicts the relationship between microbubble size and microbubble resonance frequency in accordance with various embodiments.

Referring to FIG. 2, the relationship 200 between microbubble size (e.g., mean radius, $R_0$) and microbubble resonance frequency, $f_m$, may be empirically established prior to the ultrasound procedure. As depicted, generally, the smaller the radius of the microbubbles, the larger the resonance frequency they will have. Accordingly, in some embodiments, the resonance frequency $f_m$ of the introduced microbubbles is controlled via their size distribution. For example, after the optimal frequency, $f_r$, of the ultrasound is determined as described above, the radius of microbubbles corresponding to the optimal ultrasound frequency may be computationally determined (with any necessary interpolation or extrapolation) using the established relationship 200. The size distribution of the microbubbles may then be selected such that a significant fraction (e.g., more than 50%, 90%, 95%, or 99% or more) of the microbubbles have a radius below (or, in some embodiments, above) that corresponding to a resonance frequency equal to the applied ultrasound frequency, $f_r$. In one embodiment, the maximum radius of the administered microbubbles is selected to be at least 50% smaller than the radius corresponding to a resonance frequency equal to the applied ultrasound frequency, $f_r$. This can be achieved by filtering the microbubbles with a filter having a pore size of the selected microbubble size. In another embodiment, the minimal radius of the administered microbubbles is selected to be at least 50% larger than the radius corresponding to the resonance frequency that is equal to the applied ultrasound frequency, $f_r$. Again, the filter having the pore size of the selected microbubble size may be implemented to filter the microbubbles; subsequently, the microbubbles that did not pass through the filter may be suspended in a microbubble solution for injection into the target region later.

Figure 3:
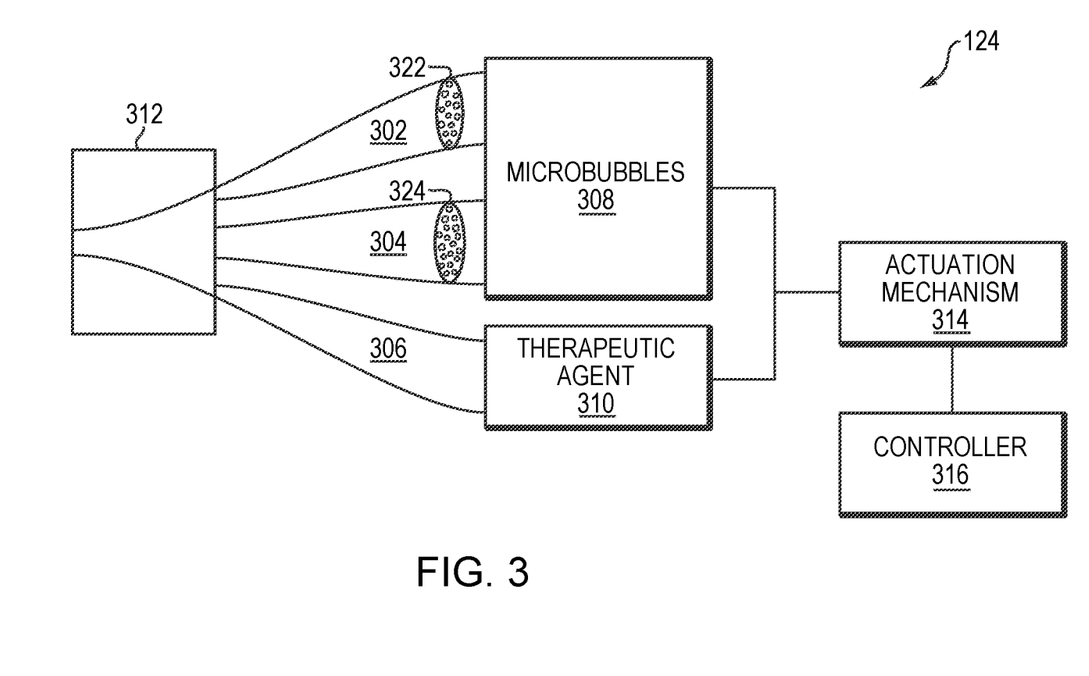
FIG. 3 depicts an exemplary administration system for introducing microbubbles to a target region in accordance with various embodiments.

In various embodiments, the filter is integrated with the administration system 124. For example, referring to FIG. 3, the administration system 124 may include one or more independent channels 302-306 fluidly coupled to one or more containers 308, 310 that store pre-formed microbubbles and/or therapeutic agents for targeted drug delivery. The channels 302-306 may then be fluidly coupled to an introducing device (e.g., a catheter or a needle) 312 for administering microbubbles and/or therapeutic agents from their corresponding channels into the patient's body. In addition, the system 124 may include an actuation mechanism (e.g., a syringe, a peristaltic pump, etc.) 314 coupled to a controller 316 for forcing the microbubbles and/or therapeutic agents through their corresponding channels into the introducing device 312 for administration to the patient. The controllers 316 may be a separate unit from the ultrasound controller 108 or may be integrated therewith as a single unit. In some embodiments, the microbubbles in the container are polydisperse in size; thus, each channel associated therewith may have a filter of a different pore size. For example, the channels 302, 304 may have filters 322, 324 with pore sizes of 0.5 μm and 2 μm, respectively. By coupling the container 308 to different channels, microbubbles having different maximum sizes may be generated. This approach is particularly useful when the condition (e.g., a size or a temperature) of the target/non-target region and/or microbubble response to the ultrasound waves/pulses changes during treatment, and adjustment of the microbubble size is desired to maintain optimal treatment effects at the target region while minimizing damage to the non-target region. In one implementation, the fluid coupling between the container 308 and the channels 302, 304 is adjusted in real time based on the monitored target/non-target condition and/or microbubble response as further described below. Configurations of the administration system 124 and one or more filters for selecting a desired size distribution of microbubbles and introducing the microbubbles into the target region 101 may be found in U.S. Patent Application No. 62/597,076, the contents of which are incorporated herein by reference.

During treatment, the therapeutic effect (e.g., tissue-permeability enhancement or ablation) on the target and/or non-target regions may be monitored using the imager 112 or other suitable device (e.g., a temperature sensor or a biosensor). In addition, the microbubble response to the applied acoustic field at the target and/or non-target regions may be monitored using the transducer 102 and/or acoustic-signal detector 122. If the therapeutic effect in the target region is below a desired target objective and/or an undesired microbubble response and/or therapeutic effect at the non-target region is detected, the determined values of the ultrasound parameters may be adjusted. For example, when the tissue permeability increase at a target BBB region is insufficient to allow penetration of a desired therapeutic agent therethrough, the ultrasound intensity may be increased and/or the sonication frequency may be reduced to cause additional microbubble cavitation, thereby disrupting the target BBB region to a satisfactory degree. Conversely, when a sensitive organ outside of the target region is disrupted, the ultrasound power may be reduced and/or the ultrasound frequency may be increased to reduce the microbubble response at the non-target region. Alternatively, the microbubble response and its energy-enhancing effect may be reduced during treatment by adjusting the resonance frequency $f_m$ of the microbubbles in the subsequent dose(s) such that it is differs further from the selected optimal ultrasound frequency $f_t$. For example, the difference between the microbubble resonance frequency $f_m$ and selected ultrasound frequency $f_t$ may be increased from a factor of ten to a factor of twenty for reducing the microbubble response to the sonications. In some embodiments, the therapeutic effect in the non-target region is substantially below the safety threshold. It may be desirable to reduce the difference between the microbubble resonance frequency $f_m$ and the selected ultrasound frequency $f_t$ (e.g., from a factor of ten to a factor of five) so as to improve treatment efficiency at the target region without compromising safety. Adjustment of the microbubble resonance frequency $f_m$ may be achieved by changing a chemical property of the microbubbles (e.g., the molecular weight or composition of the shell material) and/or computationally interpolating or extrapolating the corresponding microbubble size using the established relationship depicted in FIG. 2; subsequently, the microbubbles may be filtered with a filter having a pore size corresponding to the computed microbubble size. In this way, the treatment-enhancing effect can be altered during the treatment itself for safety or efficacy reasons. Accordingly, various embodiments of the present invention advantageously provide an approach that maximizes the therapeutic effect at the target region 101 while minimizing the damage resulting from microbubbles at the non-target region. Approaches to measuring tissue permeability during the ultrasound procedure are provided, for example, in U.S. Patent Application entitled "Cavitation-Enhanced Targeted Drug Delivery and Dosing" filed on even date herewith; approaches to monitoring the therapeutic effect on the target and/or non-target regions in real-time during the ultrasound procedure are provided, for example, in U.S. Patent Application No. 62/597,073 (filed on Dec. 11, 2017); approaches to measuring the microbubble response to the applied acoustic field are provided, for example, in International Application No. PCT/US18/33815 (filed on May 22, 2018); and approaches to configuring the transducer array for detecting the microbubble response are provided, for example, in U.S. Patent Application No. 62/681,282 (filed on Jun. 6, 2018). The contents of these applications are incorporated herein by reference.

In some embodiments, the ultrasound treatment is performed in combination with other therapeutic methods, such as radiation therapy or targeted drug delivery. For example, the ultrasound-induced microbubble oscillation/cavitation may disrupt vascular tissue in the target region 101; this allows a radiation dose in the radiation therapy to be significantly reduced while still achieving a desired efficiency of the treatment. Approaches to combining the ultrasound and radiation therapy are provided, for example, in U.S. patent application Ser. No. 15/637,163, filed on Jun. 29, 2017, the contents of which are incorporated herein by reference. In another treatment scenario, the ultrasound-induced microbubble oscillation/cavitation may increase the tissue permeability at the target region; this allows a higher dose of therapeutic agent to reach the target tissue, thereby enhancing the therapeutic effect.

Figure 4:
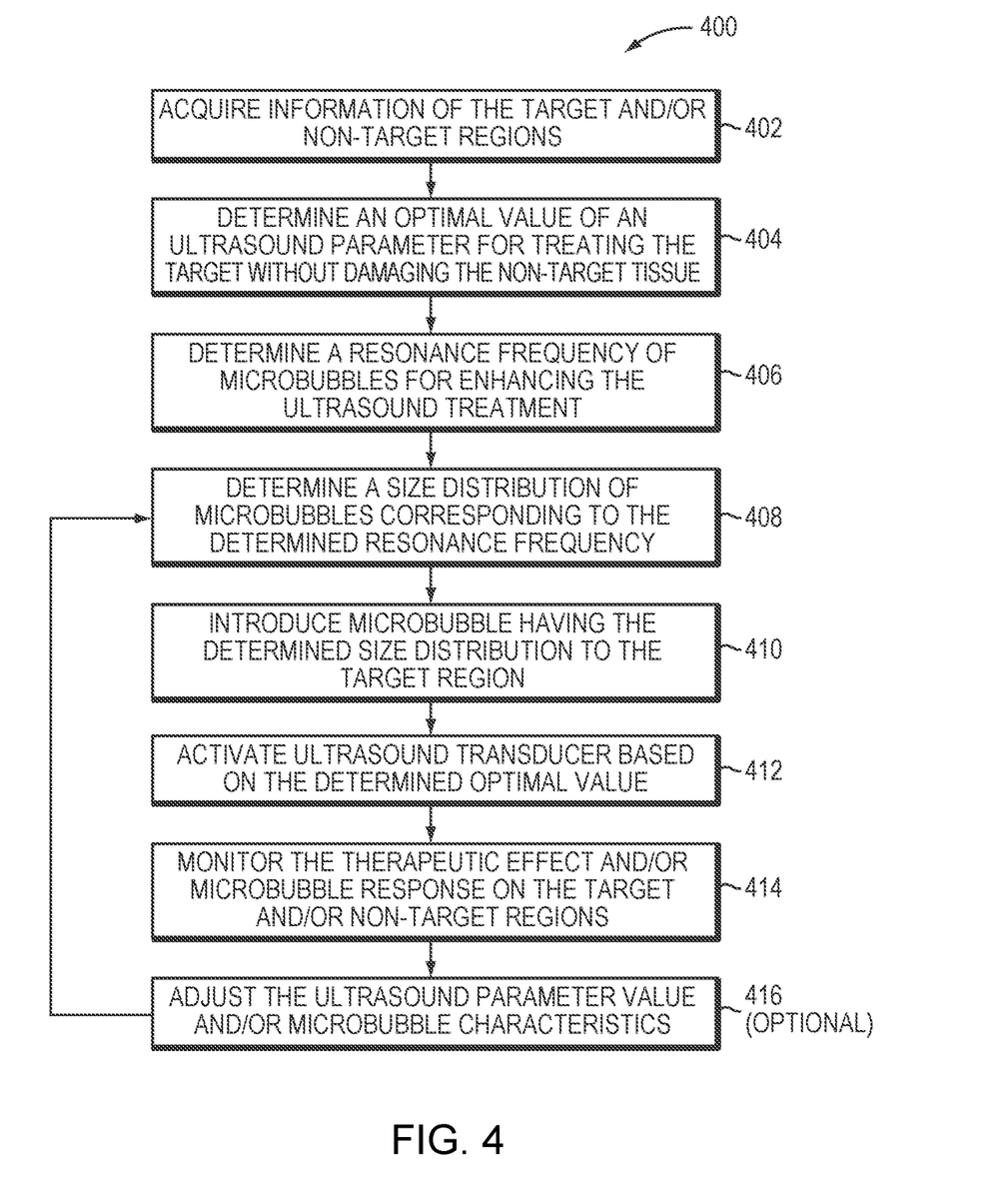
FIG. 4 is a flow chart illustrating an approach to utilizing microbubbles to enhance ultrasound treatment and/or targeted drug delivery in accordance with various embodiments of the present invention.

FIG. 4 illustrates a representative approach 400 using microbubbles to enhance ultrasound treatment and/or targeted drug delivery while limiting damage to non-target tissue in accordance with various embodiments. In a first step 402, an imager (e.g., an MRI device) 112 is utilized to acquire information (such as the location, size, shape, type, property, structure, thickness, density, etc.) of the target region and/or non-target region. In a second step 404, based at least in part on the information acquired using the imager, the optimal value of one or more ultrasound parameters (e.g., frequency, amplitude, phase) associated with the ultrasound transducer can be determined using a physical model. Additionally or alternatively, the optimal value(s) of the ultrasound parameter(s) may be empirically determined prior to the ultrasound procedure. In a third step 406, based on the determined optimal value(s) of the ultrasound transducer, a microbubble characteristic (e.g., a resonance frequency) may be determined for enhancing the ultrasound treatment. Preferably, the microbubble resonance frequency is substantially larger than the ultrasound frequency (e.g., by a factor of ten), but it can be substantially smaller than the ultrasound frequency, if desired. In a fourth step 408, a size distribution of the microbubbles corresponding to the determined resonance frequency may be determined using, for example, an established relationship therebetween. In a fifth step 410, microbubbles having the determined size distribution may then be introduced to the target region. In a sixth step 412, the ultrasound transducer may be activated based on the determine optimal value(s) to perform the treatment. During the treatment, the therapeutic effect and/or microbubble response at the target/non-target regions may be monitored (in a seventh step 414). If the therapeutic effect in the target region is below a desired target objective and/or an undesired microbubble response and/or therapeutic effect at the non-target region is detected, the ultrasound parameter value(s) and/or microbubble characteristic may be adjusted. Steps 408-414 may be iteratively performed throughout the entire ultrasound procedure.

In general, functionality for utilizing microbubbles to enhance ultrasound treatment and/or targeted drug delivery while limiting damage to non-target tissue may be structured in one or more modules implemented in hardware, software, or a combination of both, whether integrated within a controller of the imager 122, an ultrasound system 100 and/or the administration system 124, or provided by a separate external controller or other computational entity or entities. Such functionality may include, for example, analyzing imaging data of the target and/or non-target regions acquired using an imager 112, determining the optimal value(s) of ultrasound parameter(s) empirically and/or using the imaging data, establishing a relationship between a microbubble size distribution and a microbubble resonance frequency, determining a microbubble resonance frequency and its corresponding microbubble size distribution based on the optimal ultrasound parameter value(s), causing the microbubble having the determined size distribution to be introduced to the target region, causing the ultrasound transducer to be activated using the determine optimal parameter value(s), monitoring the therapeutic effect and/or microbubble response at the target/non-target regions during the ultrasound procedure, and/or adjusting the optimal ultrasound parameter value(s) and/or microbubble resonance frequency as described above.

In addition, the ultrasound controller 108 and/or the administration system controller 316 may include one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The therapeutic agent may include any drug that is suitable for treating a tumor. For example, for treating glioblastoma (GBM), the drug may include or consist of, e.g., one or more of Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, Cytarabine (cytosine arabinoside, ara-C)/ara-U, etc.

In addition, for treating GBM, those skilled in the art can select a drug and a BBB opening regime optimized to enhance drug absorption across the BBB within patient safety constraints. In this regard, it is known that the BBB is actually already disrupted in the core of many tumors, allowing partial penetration of antitumor drugs; but the BBB is widely intact around the "brain adjacent to tumor" (BAT) region where invasive/escaping GBM cells can be found, and which cause tumor recurrence. Overcoming the BBB for better drug delivery within the tumor core and the BAT can be accomplished using ultrasound as described herein. The drugs employed have various degrees of toxicity and various penetration percentages through the BBB. An ideal drug has high cytotoxicity to the tumor and no BBB penetration (so that its absorption and cytotoxic effects can be confined to regions where the BBB is disrupted), low neurotoxicity (to avoid damage to the nervous system), and tolerable systemic toxicity (e.g., below a threshold) at the prescribed doses. The drug may be administered intravenously or, in some cases, by injection proximate to the tumor region.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for enhancing treatment of target tissue while limiting damage to non-target tissue, the system comprising:
   an ultrasound transducer;
   an administration device for providing microbubbles having a first size distribution to the target tissue; and
   a controller configured to:
      (a) select a frequency of ultrasound waves transmitted from the ultrasound transducer for generating a focus in the target tissue;
      (b) determine the first size distribution of the microbubbles such that at least 50% of the microbubbles have a radius different from a critical radius corresponding to a resonance frequency matching the selected frequency of ultrasound waves; and
      (c) cause the ultrasound transducer to transmit the ultrasound waves at the selected frequency for treating the target tissue.

2. The system of claim 1, wherein the administration device further comprises a filter having a pore size different from the critical radius.

3. The system of claim 1, wherein at least 99% of the provided microbubbles have a radius smaller than the critical radius.

4. The system of claim 1, wherein a maximal radius of at least 50% of the provided microbubbles is at least 50% smaller than the critical radius.

5. The system of claim 1, wherein a maximal radius of at least 99% of the provided microbubbles is at least 50% smaller than the critical radius.

6. The system of claim 1, wherein at least 99% of the provided microbubbles have a radius larger than the critical radius.

7. The system of claim 1, wherein a minimal radius of at least 50% of the provided microbubbles is at least 50% larger than the critical radius.

8. The system of claim 1, wherein a minimal radius of at least 99% of the provided microbubbles is at least 50% larger than the critical radius.

9. The system of claim 1, further comprising an imaging device for acquiring characteristics of the target tissue and non-target tissue, the controller being responsive to signals from the imaging device indicative of the characteristics and being configured to select the frequency based on the signals.

10. The system of claim 9, wherein the non-target tissue comprises intervening tissue located between the source of focused ultrasound and the target tissue, the controller being further configured to (i) predict acoustic interactions between the ultrasound waves and the intervening tissue based on the acquired characteristics and (ii) select the frequency of ultrasound waves based at least in part on the predicted acoustic interactions.

11. The system of claim 1, wherein the controller is further configured to:
   (i) cause the ultrasound transducer to sonicate the target tissue with a plurality of ultrasound frequencies within a test range;
   (ii) measure, for each frequency, a value of a parameter indicative of an amount of ultrasound energy deposited in the target tissue; and
   (iii) select the frequency of ultrasound waves among the frequencies within the test range based on the measured values.

12. The system of claim 11, wherein the controller is further configured to select the frequency of ultrasound waves corresponding to the measured value that itself corresponds to a maximum amount of ultrasound energy deposited in the target tissue.

13. The system of claim 11, wherein the parameter comprises at least one of a power, an energy, an intensity, an acoustic force, a tissue displacement, or a temperature.

14. The system of claim 11, further comprising at least one of an imaging device or an acoustic signal detector for measuring the value of the parameter.

15. The system of claim 1, wherein the controller is further configured to determine a frequency range such that the selected frequency is therewithin.

16. The system of claim 15, wherein the provided microbubbles having the first size distribution where at least 50% of the microbubbles have a radius smaller than a minimal radius corresponding to a maximal frequency within the frequency range.

17. The system of claim 15, wherein the provided microbubbles having the first size distribution where at least 50% of the microbubbles have a radius larger than a maximal radius corresponding to a minimal frequency within the frequency range.

18. The system of claim 1, further comprising a detector for detecting an acoustic signal from the microbubbles, wherein the controller is further configured to determine, based on the detected acoustic signal, whether a microbubble response to the ultrasound waves is above a predetermined threshold, and if so, to adjust at least one of the selected frequency or an intensity associated with the ultrasound waves.

19. The system of claim 1, further comprising a detector for detecting an acoustic signal from the microbubbles, wherein the controller is further configured to determine, based on the detected acoustic signal, whether a microbubble response to the ultrasound waves is above a predetermined threshold, and if so, to cause the administration device to provide microbubbles having a second size distribution, radiuses of the microbubbles in the second size distribution being smaller than radiuses of the microbubbles in the first size distribution.

20. The system of claim 1, further comprising a detector for detecting an acoustic signal from the microbubbles, wherein the controller is further configured to determine, based on the detected acoustic signal, whether a microbubble response to the ultrasound waves is above a predetermined threshold, and if so, to cause the administration device to provide microbubbles having a second size distribution, radiuses of the microbubbles in the second size distribution being larger than radiuses of the microbubbles in the first size distribution.

21. The system of claim 1, further comprising a radiation device for transmitting a radiation dose to the target tissue for treatment.

22. The system of claim 1, wherein the administration device is further configured to administer a therapeutic agent to the target tissue for treatment.

23. The system of claim 22, wherein the therapeutic agent comprises at least one of Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, or Cytarabine (cytosine arabinoside, ara-C)/ara-U.

* * * * *